(12) United States Patent
Shin et al.

(10) Patent No.: US 6,559,320 B2
(45) Date of Patent: May 6, 2003

(54) PROCESS FOR PREPARING 4-SUBSTITUTED 1H-PYRROLE-3-CARBOXYLIC ACID ESTER

(75) Inventors: Hyun Ik Shin, Taejon (KR); Sung Tak Oh, Taegu (KR); Jay Hyok Chang, Taejon (KR); Kyoo Woong Lee, Taejon (KR)

(73) Assignee: LG Chem Investment Ltd., Seoul (KR)

( * ) Notice: Subject to any disclaimer, the term of this patent is extended or adjusted under 35 U.S.C. 154(b) by 0 days.

(21) Appl. No.: 10/204,579

(22) PCT Filed: Feb. 12, 2001

(86) PCT No.: PCT/KR01/00201

§ 371 (c)(1), (2), (4) Date: Aug. 22, 2002

(87) PCT Pub. No.: WO01/62727

PCT Pub. Date: Aug. 30, 2001

(65) Prior Publication Data

US 2003/0069432 A1 Apr. 10, 2003

(30) Foreign Application Priority Data

Feb. 22, 2000 (KR) .......................................... 2000/8452

(51) Int. Cl.[7] .............................................. C07D 207/36
(52) U.S. Cl. ....................................................... 548/531
(58) Field of Search ......................................... 548/531

(56) References Cited

PUBLICATIONS

Pauvi, "An Efficient Method for the Synthesis, Etc" J. Org Chem, 1997, 62, 2649–2651.*

* cited by examiner

Primary Examiner—Patricia L. Morris
(74) Attorney, Agent, or Firm—Peter F. Corless; Christine C. O'Day; Edwards & Angell, LLP

(57) ABSTRACT

The present invention relates to a novel process for preparing pyrrole ester compounds, which are key intermediates in the preparation of farnesyl transferase inhibitors, an anticancer agent Horner-Emmons reaction of aldehyde compounds provides the corresponding α,β-unsaturated esters, which without any separation and/or purification steps, are treated with toluenesutfonyl-methylisocyanate in the presence of base to give pyrrole esters in one-pot fashion.

10 Claims, No Drawings

PROCESS FOR PREPARING 4-SUBSTITUTED 1H-PYRROLE-3-CARBOXYLIC ACID ESTER

TECHNICAL FIELD

The present invention relates to a novel process for preparing pyrrole ester compounds which are key intermediate in the preparation of farnesyl transferase inhibitors, an anti-cancer agent (see: Ko, J. S. et al., WO 9928315). Horner-Emmons reaction of aldehyde compounds provides the corresponding α,β-unsaturated esters, which without any separation and/or purification steps, are treated with toluenesulfonylmethylisocyanate (TosMIC: hereinafter referred to as 'TosMIC') in the presence of base to give pyrrole esters in one-pot fashion.

BACKGROUND ART

The most typical method for the synthesis of 3-substituted-4-pyrrole ester compound is through the cyclization reaction of an isonitrile compound with an electrophilic α,β-unsaturated compound, as depicted in the following Reaction Scheme 1. As isonitrile part, TosMIC is the most well known reagent (van Leusen, A. M. et.al. *Teiahedron Leit.* 1972, 52, 5337.).

Reaction Scheme 1

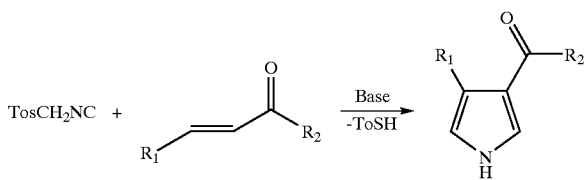

in which

R$_1$ and R$_2$ independently of one another represent C$_1$–C$_4$-alkyl.

Recently BetMIC (Katrizky, A. R. et.al. *Heterocycles*, 1997, 44, 67.) of the following formula showing a similar reactivity to TosMIC has been developed.

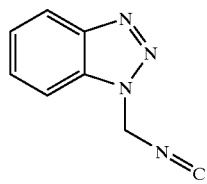

Thereafter, the same researcher has developed a new method as depicted in the following Reaction Scheme 2. TosMIC is reacted with a carbonyl compound in the presence of a base and POCl$_3$(phosphorous oxychloride) in sequence to give an α,β-unsaturated isonitrile compound, which is then reacted with an activated nucleophile to give a pyrrole compound (van Leusen, A. M. et.al. *J Org. Chem.* 1992, 57, 2245.).

Reaction Scheme 2

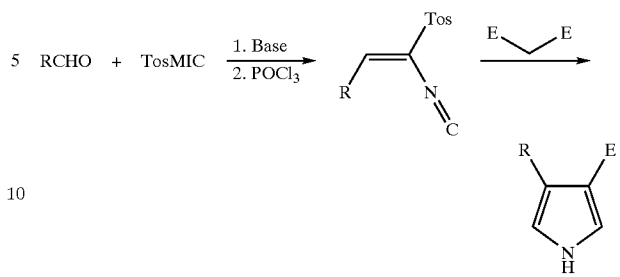

in which

R represents alkyl, allyl, or aryl, and

E represents an electron-withdrawing group.

As known in the previous arts, the general synthesis of 3-substituted-4-pyrrole ester contains two discrete stages. The first stage is the preparation and purification of α,β-unsaturated compound and the second stage is the cyclization reaction of the purified α,β-unsaturated compound with TosMIC in the presence of base. However, since the conventional method requires purification step after the preparation of α,β-unsaturated compound, it is inevitable to efflux the reaction solvent as waste unless it is recycled. To remove the efflux of waste solvent and increase the efficiency of the process, it is proposed to run the two reactions in the same solvent as one-pot fashion.

DISCLOSURE OF INVENTION

Under the technical background as explained above, the present inventors have investigated extensively on the eradication of the waste solvent problem and the increase of the efficiency of the process for the purpose of mass production of pyrrole ester. As a result, we have come up with the present invention by combining the two stages of the pyrrole synthesis into one-pot/one stage process. Therefore, the pyrrole ester is obtained in high purity and in environmentally friendly manner.

The object of the present invention is to provide a process for preparing a desired pyrrole ester derivative represented by the following formula (1):

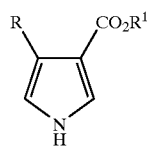

(1)

in which

R represents alkyl, allyl, or aryl, and

R$^1$ represents C$_1$–C$_4$-alkyl, by reacting an aldehyde compound represented by the following formula (2):

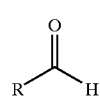

(2)

in which R is defined as previously described, with a trialkylphosphonoacetate represented by the following formula (3):

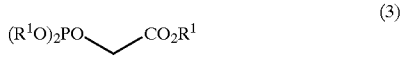
(3)

in which $R^1$ is defined as previously described, in an inert solvent in the presence of an alkali metal alkoxide base in an amount of 1 to 1.5 molar equivalent with respect to the compound of formula (2) to give an α,β-unsaturated ester compound represented by the following formula (4):

(4)

in which R and $R^1$ are defined as previously described, and subsequently by adding TosMIC and the same base as used in the previous step in an amount of 1 to 1.5 molar equivalent with respect to the compound of formula (2).

BEST MODE FOR CARRYING OUT THE INVENTION

The process according to the present invention is depicted in the following Reaction Scheme 3

Reaction Scheme 3

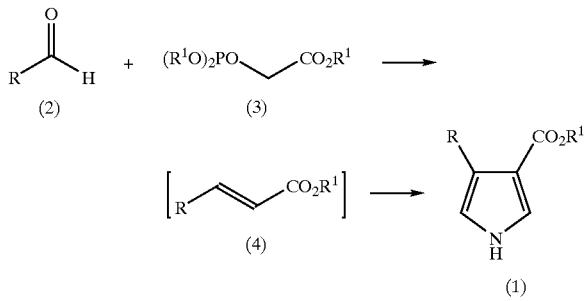

In the process of the present invention, it is very important to use the alkali metal alkoxide base in an amount of 1 to 1.5 molar equivalents with respect to the compound of formula (2). If the amount of base is deviated from the defined range, the reaction to prepare the unsaturated ester compound of formula (4) is not proceeded cleanly. As a result, the object of the present invention to react the unsaturated ester compound directly in the next step in the same reaction system without being separated cannot be achieved. As the base which can be used for such a purpose, alkali metal methoxide, -ethoxide, -t-butoxide, -t-pentoxide, etc., preferably sodium- or potassium-t-butoxide or -t-pentoxide can be used. Though the reaction is well proceeded by using the base in an amount of 1 to 1.5 molar equivalents, however, 1 to 1.3 molar equivalent thereof may be sufficient to exhaust the aldehyde compound. Further, an excess base may cause hydrolysis in the subsequent separation step of layers, it is preferable to use the base in an amount of 1 to 1.3 molar equivalent in order to minimize such a hydrolysis reaction.

Any inert solvent which does not adversely affect to the reaction can be used in the process according to the present invention, but tetrahydrofuran, dimethoxyethane, toluene or mixtures thereof is preferably used.

After the process for preparing the compound of formula (4) is completed, TosMIC and the same base as used in the previous reaction step were added and stirred until the α,β-unsaturated ester is completely removed to produce the pyrrole ester compound of formula (1). In this reaction, TosMIC is added in an amount of 1 to 1.3 molar equivalent with respect to the compound of formula (2) and the base is added in an amount fallen under the same range as mentioned in the previous step of preparing the compound of formula (4). Then, the reaction solution is quenched with water and extracted with a suitable extracting solvent which is not miscible with water at temperature of 40 to 90° C. (if a high yield is desired, 60 to 90° C. is preferable). The organic layer was separated and stirred at room temperature, and the formed precipitate is filtered to give the desired compound of formula (1) in a pure state. The solvent is not always required to remove before carrying out the extraction. But, in case of tetrahydrofuran or dimethoxyethane is used as the reaction solvent, since they are well miscible with water, it is required to be removed by distillation. Therefore, the increase of yield can be expected if the solvent is removed in advance by distillation under reduced pressure before the extraction. As the extracting solvent for this purpose, toluene or n-butyl acetate can be preferably used. Particularly, when sodium-t-pentoxide is used as the base, since this base is well soluble in the preferable extracting solvent toluene, the trouble to have to use an extracting solvent different from the reaction solvent may be saved.

The reaction for preparing the compound of formula (4) is proceeded at temperature ranging from −20 to 40° C., preferably 10 to 25° C. on a satisfactory level. Also, the process for producing the desired pyrrole ester derivative of formula (1) from the compound of formula (4) thus obtained is suitably carried out at temperature ranging from 0 to 40° C.

Contrary to the prior arts, after the unsaturated ester compound of formula (4) is produced, it directly reacts with TosMIC without any separation or purification, in the present invention to afford the pyrrole ester. Thus, reduction of the waste solvent and enhancement of the efficiency of the process is obvious and provides great advantage particularly when the process is applied on an industrial production.

The present invention will be more specifically explained in the following examples. However, it should be understood that they are intended to illustrate the present invention but not in any manner to limit the scope of the present invention.

EXAMPLE 1

Synthesis of ethyl 4-(naphthalen-1-yl)-1H-pyrrole-3-carboxylic acid ester

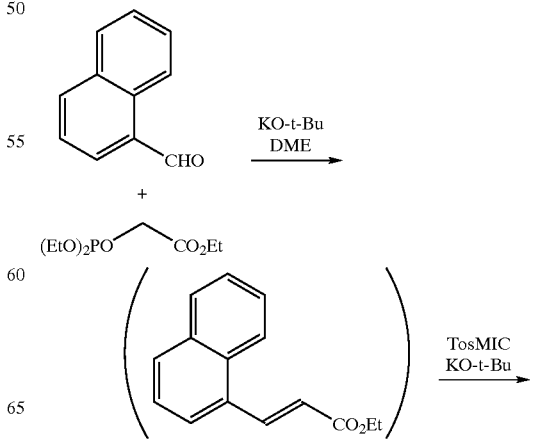

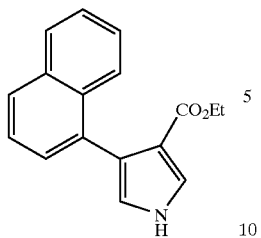

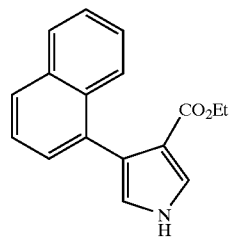

1-Naphthaldehyde(35 g, 0.224 mol) and triethylphosphonoacetate(50 g, 0.224 mol) were mixed under nitrogen atmosphere, 180 ml of dimethoxyethane (DME) was added, and the resulting mixture was cooled to 0° C. under a thorough stirring. To this solution was added slowly potassium-t-butoxide(30 g, 1.2 molar equivalent) while maintaining reaction temperature below 20° C. After confirming the complete removal of 1-naphthaldehyde by HPLC, TosMIC(52.5 g, 1.2 molar equivalent) and potassium-l-butoxide(32 g, 1.3 molar equivalent) were added slowly in sequence maintaining the reaction temperature below 20° C. After confirming the exhaustion of α,β-unsaturated ester by HPLC, 70 ml of distilled water was added and DME was removed therefrom by distillation under reduced pressure. 200 ml of toluene was added to this concentrate. The mixture was warmed and extracted with 350 ml of distilled water. The separated organic layer was subjected to azeotropic distillation to remove the residual moisture. The concentrate was cooled with slow stirring to room temperature and the formed solid was filtered. The filter cake was washed twice with 30 ml of cold toluene, twice with 50 ml of distilled water, and dried to give 37 g (HPLC Purity 95.2%, Yield 61%) of the title compound as a white powder.

$^1$H NMR(CDCl$_3$, ppm) δ 8.65(1H, br, s), 7.80(3H, m), 7.59(1H, dd, J1=3.2 Hz, J2=2.3 Hz), 7.41(4H, m), 6.79(1H, t, J=2.3 Hz), 3.91(2H, q, J=6.9 Hz), 0.71(3H, t, J=6.9 Hz) 13C NMR(CDCl3, ppm) δ 165.2, 133.8, 133.51, 133.50, 128.0, 127.5, 127.3, 126.7, 125.5, 125.4, 125.2, 124.7, 123.9, 119.3, 115.9, 59.5, 13.7.

m.p.(not calibrated) 164–165° C.

EXAMPLE 2

Synthesis of ethyl 4-(naphthalen-1-yl)-1H-pyrrole-3-carboxylic acid ester

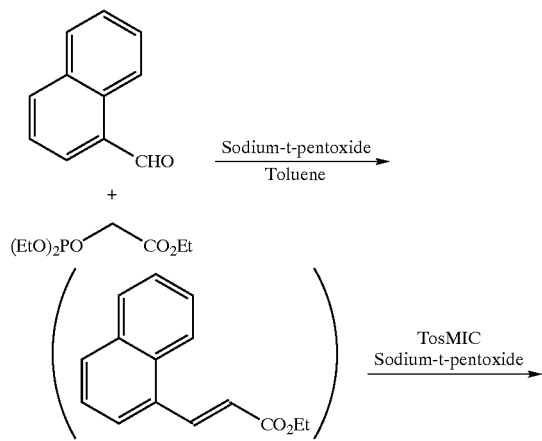

1-Naphthaldehyde(28 g, 0.18 mol) and triethylphosphonoacetate (40.35 g, 0.18 mol) were introduced into 500 mL round bottom flask and diluted with 180 ml of toluene. The reaction misture was cooled to about 0 to 5° C. and sodium-t-pentoxide (23.8 g, 0.216 mol) was added slowly in order to maintain the reaction temperature below 20° C. After the addition was completed, the reaction mixture was stirred for 1 to 2 hours at room temperature and cooled again to 0 to 5° C. TosMIC(36.9 g, 0.189 mol) and sodium-t-pentoxide(23.8 g, 0.216 mol) were added slowly in sequence maintaining the reaction temperature below 20° C. After the addition was completed, the reaction mixture was stirred for 3 to 6 hours at room temperature and 250 ml of distilled water was added. The resulting mixture was heated at about 70° C. and the organic layer was separated, washed once again with 250 ml of distilled water at the same temperature. The separated organic layer was subjected to azeotropic distillation to remove the residual moisture. Then, the concentrate was cooled to about 50° C. with slow stirring. After the crystal was precipitated, the reaction temperature was lowered to 0 to 5°C. and further stirred. The formed solid was filtered, washed twice with 30 ml of toluene and dried under nitrogen to give 29.6 g (HPLC Purity 96%PAR, Yield 62%) of the title compound as a white powder.

INDUSTRIAL APPLICABILITY

According to the process of the present invention, the pyrrole ester compounds of formula (1), key intermediates for preparing farnesyl transferase inhibitors, an anti-cancer agent, can be prepared with a high purity and yield on an industrial scale.

What is claimed is:

1. A process for preparing a pyrrole ester derivative represented by the following formula (1):

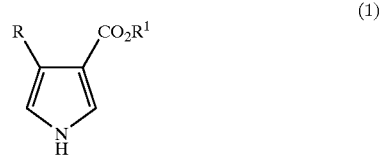

in which

R represents alkyl, allyl, or aryl, and $R^1$ represents $C_1$–$C_4$-alkyl, characterized by reacting an aldehyde compound represented by the following formula (2):

(2)

in which R is defined as previously described, with a trialkylphosphonoacetate represented by the following formula (3):

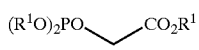

(3)

in which $R^1$ is defined as previously described, in an inert solvent in the presence of an alkali metal alkoxide base in an amount of 1 to 1.5 molar equivalent with respect to the compound of formula (2) to give an α,β-unsaturated ester compound represented by the following formula (4):

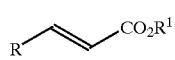

(4)

in which R and $R^1$ are defined as previously described, and subsequently by adding TosMJC and the same base as used in the previous step in an amount of 1 to 1.5 molar equivalent with respect to the compound of formula (2).

2. The process of claim 1 wherein the alkali metal alkoxide base is used in an amount of 1 to 1.3 molar equivalent with respect to the compound of formula (2).

3. The process of claim 1 or 2 wherein the alkali metal alkoxide base is sodium- or potassium-t-butoxide or -t-pentoxide.

4. The process of claim 1 wherein the inert solvent is tetrahydrofuran, dimethoxyethane, toluene or mixtures thereof.

5. The process of claim 1 wherein TosMIC is used in an amount of 1 to 1.3 molar equivalent with respect to the compound of formula (2).

6. The process of claim 1 wherein the process for preparing the compound of formula (4) is carried out at temperature ranging from −20 to 40° C., and the process for preparing the compound of formula (1) is carried out at temperature ranging from 0 to 40° C.

7. The process of claim 6 wherein the process for preparing the compound of formula (4) is carried out at temperature ranging from 10 to 25° C.

8. The process of claim 1 wherein the compound of formula (1) is prepared and extracted with an organic solvent further added, the organic layer is separated, and the compound of formula (1) is recrystallized therefrom.

9. The process of claim 8 wherein the organic solvent is toluene or n-butyl acetate.

10. The process of claim 8 or 9 wherein the extraction is carried out at temperature ranging from 40 to 90° C.

* * * * *